(12) United States Patent
Sansonetti et al.

(10) Patent No.: US 7,396,812 B2
(45) Date of Patent: Jul. 8, 2008

(54) METHOD FOR MODULATING NOD1 ACTIVITY, USE OF A MTP RELATED MOLECULE FOR MODULATING NOD1 ACTIVITY, AND THERAPEUTIC APPLICATIONS THEREOF

(75) Inventors: Philippe Sansonetti, Paris (FR); Stephen Girardin, Vincennes (FR); Dana Philpott, Vincennes (FR); Ivo Boneca, Vitry sur Seine (FR)

(73) Assignees: Institut Pasteur, Paris (FR); Institut National de la Sante et de la Recherche Medicale, Paris (FR)

( * ) Notice: Subject to any disclaimer, the term of this patent is extended or adjusted under 35 U.S.C. 154(b) by 319 days.

(21) Appl. No.: 10/551,040

(22) PCT Filed: Mar. 29, 2004

(86) PCT No.: PCT/IB2004/001318

§ 371 (c)(1),
(2), (4) Date: Sep. 27, 2005

(87) PCT Pub. No.: WO2004/086039

PCT Pub. Date: Oct. 7, 2004

(65) Prior Publication Data

US 2006/0217319 A1    Sep. 28, 2006

Related U.S. Application Data

(60) Provisional application No. 60/457,572, filed on Mar. 27, 2003.

(51) Int. Cl.
*A61K 38/06* (2006.01)
(52) U.S. Cl. .......................................... 514/2; 530/331
(58) Field of Classification Search ....................... None
See application file for complete search history.

(56) References Cited

U.S. PATENT DOCUMENTS

2002/0197693 A1   12/2002   Bertin

OTHER PUBLICATIONS

PCT/IB2004/001318 International Preliminary Report on Patentability, mailed Oct. 13, 2005.
Akira et al., "Toll-like receptors: critical proteins linking innate and acquired immunity", *Nature Immunology*, vol. 2, No. 8, pp. 675-680 (2001).
Askew et al., "Molecular Recognition with Convergent Functional Groups. 6. Synthetic and Structural Studies with a Model Receptor for Nucleic Acid Components", *J. Am. Chem. Soc.*, vol. 111, pp. 1082-1090 (1989).
Bertin et al., "Human CARD4 Protein Is a Novel CED-4/Apaf-1 Cell Death Family Member That Activates NF-κB", *The Journal of Biological Chemistry*, vol. 274, No. 19, pp. 12955-12958 (1999).

Blackburn et al., "Identification of Four Families of Peptidoglycan Lytic Transglycosylases", *Journal of Molecular Evolution*, vol. 52, pp. 78-84 (2001).
Carballo et al., "Elucidation of the structure of an alanine-lacking core tetrasaccharide trisphosphate from the lipopolysaccharide of *Pseudomonas aeruginosa* mutant H4", *Eur. J. Biochem.*, vol. 261, pp. 500-508 (1999).
Chin et al., "Involvement of receptor-interacting protein 2 in innate and adaptive immune responses", *Nature*, vol. 416, pp. 190-194 (2002).
Choe et al., "Requirement for a Peptidoglycan Recognition Protein (PGRP) in Relish Activation and Antibacterial Immuune Responses in *Drosophila*", *Science*, vol. 296, pp. 359-362 (2002).
De Jonge et al., "Peptidoglycan Composition of a Highly Methicillin-resistant *Staphylococcus aureus* Strain", *The Journal of Biological Chemistry*, vol. 267, No. 16, pp. 11248-11254 (1992).
Eckmann et al., "Analysis by High Density cDNA Arrays of Altered Gene Expression in Human Intestinal Epithelial Cells in Response to Infection with the Invasive Enteric Bacteria *Salmonella*", *The Journal of Biological Chemistry*, vol. 275, No. 19, pp. 14084-14094 (2000).
Girardin et al., "CARD4/NOD1 mediates NF-κB and JNK activation by invasive *Shigella flexneri*," *EMBO Reports*, vol. 2, No. 8, pp. 736-742 (2001).
Girardin et al., "Nod2 Is a General Sensor of Peptidoglycan through Muramyl Dipeptide (MDP) Detection", *The Journal of Biological Chemistry*, vol. 278, No. 11, pp. 8869-8872 (2003).
Girardin et al., "Peptidoglycan Molecular Requirements Allowing Detection by Nod1 and Nod2", *The Journal of Biological Chemistry*, vol. 278, No. 43, pp. 41702-41708 (2003).
Glauner, "Separation and Quantification of Muropeptides with High-Performance Liquid Chromatography", *Analytical Biochemistry*, vol. 172, pp. 451-464 (1988).
Gottar et al., "The *Drosophila* immune response against Gram-negative bacteria is mediated by a peptidoglycan recognition protein" *Nature*, vol. 416, pp. 640-644 (2002).
Hayashi et al., "A Rapid Determination of Sodium Dodecyl Sulfate with Methylene Blue", *Analytical Biochemistry*, vol. 67, pp. 503-506 (1975).
Hayashi et al., "The innate immune response to bacterial flagellin is mediated by Toll-like receptor 5", *Nature*, vol. 410, pp. 1099-1103 (2001).
Höltje et al., "Growth of the Stress-Bearing and Shape-Maintaining Murein Sacculus of *Escherichia coli*", *Microbiology and Molecular Biology Reviews*, vol. 62, No. 1, pp. 181-203 (1998).
Hugot et al., "Association of NOD2 leucine-rich repeat variants with susceptibility to Crohn's disease", *Nature*, vol. 411, pp. 599-603 (2001).

(Continued)

*Primary Examiner*—Christopher R. Tate
*Assistant Examiner*—Jennifer I Harle
(74) *Attorney, Agent, or Firm*—Finnegan, Henderson, Farabow, Garrett & Dunner, L.L.P.

(57) ABSTRACT

A method for modulating Nod1 activity wherein said method comprises the steps of providing cells expressing a functional Nod1; and bringing said cells into contact with a molecule related to compositions comprising a molecule related to MTP and use of a molecule related to MTP for modulating inflammation and/or apoptosis.

15 Claims, 9 Drawing Sheets

OTHER PUBLICATIONS

Inohara et al., "An Induced Proximity Model for NF-κB Activation in the Nod1/RICK and RIP Signaling Pathways", *The Journal of Biological Chemistry*, vol. 275, No. 36, pp. 27823-27831 (2000).

Inohara et al., "Host Recognition of Bacterial Muramyl Dipeptide Mediated through NOD2", *The Journal of Biological Chemistry*, vol. 278, No. 8, pp. 5509-5512 (2003).

Inohara et al., "Human Nod1 Confers Responsiveness to Bacterial Lipopolysaccharides", *The Journal of Biological Chemistry*, vol. 276, No. 4, pp. 2551-2554 (2001).

Inohara et al., "Nod1, an Apaf-1 like Activator of Caspase-9 and Nuclear Factor κB" *The Journal of Biological Chemistry*, vol. 274, No. 21, pp. 14560-14567 (1999).

Kawai et al., "Unresponsiveness of MyD88-Deficient Mice to Endotoxin", *Immunity*, vol. 11, pp. 115-122 (1999).

Kobayashi et al., "RICK/Rip2/CARDIAK mediates signalling for receptors of the innate and adaptive immune systems", *Nature*, vol. 416, pp. 194-199 (2002).

Lee et al., "Two Lipoproteins Extracted from *Escherichia coli* K-12 LCD25 Lipopolysaccharide Are the Major Components Responsible for Toll-Like Receptor 2-Mediated Signaling", *The American Association of Immunologies*, vol. 168, pp. 4012-4017 (2002).

Lemaitre et al., "The Dorsoventral Regulatory Gene Cassette *spätzle/Toll/cactus* Controls the Potent Antifungal Response in Drosophila Adults", *Cell*, vol. 86, pp. 973-983 (1996).

Lewis et al., "Automated site-directed drug design: the concept of spacer skeletons for primary structure generation" *Proc. R. Soc. Lond.*, vol. B236, pp. 125-140 (1989).

Lewis et al., "Automated site-directed drug design: the formation of molecular templates in primary structure generation", *Proc. R. Soc. Lond.*, vol. B236, pp. 141-162 (1989).

McKinlay et al., "Rational Design of Antiviral Agents", *Ann. Rev. Pharmacol. Toxicol.*, vol. 29, pp. 111-122 (1989).

McLaughlan et al., "Molecular characterization of an autolytic amidase of *Listeria* monocytogenes EGD", *Microbiology*, 144, pp. 1359-1367 (1998).

Medzhitov, "Toll-Like Receptors And Innate Immunity", *Nature Immunology*, vol. 1, pp. 135-145 (2001).

Michel et al., "*Drosophila* Toll is activated by Gram-positive bacteria through a circulating peptidoglycan recognition protein", *Nature*, vol. 414, pp. 756-759 (2001).

Ogura et al., "A frameshift mutation in NOD2 associated with susceptibility to Crohn's disease", *Nature*, vol. 411, pp. 603-606 (2001).

Ogura et al., "Nod2, a Nod1/Apaf-1 Family Member That Is Restricted to Monocytes and Activates NF-κB", *The Journal of Biological Chemistry*, vol. 276, No. 7, pp. 4812-4818 (2001).

Pédron et al., "The Invasive Phenotype of *Shigella flexneri* Directs a Distinct Gene Expression Pattern in the Human Intestinal Epithelial Cell Line Caco-2", *The Journal of Biological Chemistry*, vol. 278, No. 36, pp. 33878-33886 (2003).

Perry et al., "The Use of 3D Modelling Databases for Identifying Structure Activity Relationships", *Quantitative Structure-Activity Relationships in Drug Design*, pp. 189-193 (1989).

Philpott et al., "Invasive *Shigella flexneri* Activates NF-κB Through a Lipopolysaccharide-Dependent Innate Intracellular Response and Leads to IL-8 Expression in Epithelial Cells", *The American Association of Immunologists*, vol. 165, pp. 903-914 (2000).

Rämet et al., "Functional genomic analysis of phagocytosis and identification of a *Drosophila* receptor for *E. coli*" *Nature*, vol. 416, pp. 644-648 (2002).

Ripka, "Computers picture the perfect drug", *New Scientist*, pp. 54-58 (1988).

Rouvinen et al., "Computer-Aided Drug Design", *Acta Pharmaceutica Fennica*, vol. 97, pp. 159-166 (1988).

Uehara et al., "Identification of MpaA, an Amidase in *Escherichia coli* That Hydrolyzes the γ-D-Glutamyl-*meso*-Diaminopimelate Bond in Murein Peptides", *Journal of Bacteriology*, vol. 185, No. 2, pp. 679-682 (2003).

| FIGURE 5A | FIGURE 5B |

Cell extracts

Immunoprecipitations (IP)

METHOD FOR MODULATING NOD1 ACTIVITY, USE OF A MTP RELATED MOLECULE FOR MODULATING NOD1 ACTIVITY, AND THERAPEUTIC APPLICATIONS THEREOF

CROSS REFERENCE TO RELATED APPLICATIONS

This application is an national phase application based on PCT/IB2004/001318, filed Mar. 29, 2004, which claims the benefit of U.S. Provisional Application No. 60/457,572, filed Mar. 27, 2003, the content of both of which is incorporated herein by reference in its entirety.

BACKGROUND OF THE INVENTION

This invention relates to the first described pathogen-recognition molecule Nod1, which senses specifically Gram-negative bacteria through a peptidoglycan motif, muramyl tripeptide. More particularly, this invention relates to the modulation of Nod1 activity by a molecule related to the muramyl tripeptide (MTP). The invention also relates to a screening process for identifying a molecule capable of modulating Nod1 activity and the therapeutic use of such a molecule for modulating inflammation and/or apoptosis. The invention also relates to a new compound, which can be used for modulating inflammation and/or apoptosis or as an adjuvant agent.

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes, such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved from worms, such as *C. elegans*, to humans. In fact, invertebrate model systems have been invaluable tools in identifying and characterizing the genes that control apoptosis. Through the study of invertebrates and more evolved animals, numerous genes that are associated with cell death have been identified, but the way in which their products interact to execute the apoptotic program is poorly understood.

Caspases, a class of proteins central to the apoptotic program, are cysteine proteases having specificity for aspartate at the substrate cleavage site. These proteases are primarily responsible for the degradation of cellular proteins that lead to the morphological changes seen in cells undergoing apoptosis. For example, one of the caspases identified in humans was previously known as the interleukin-1β (IL-1β) converting enzyme (ICE), a cysteine protease responsible for the processing of pro-IL-1β to the active cytokine.

Many caspases and proteins that interact with caspases possess domains of about 60 amino acids called a Caspase Recruitment Domain (CARD). Others have postulated that certain apoptotic proteins bind to each other via their CARDs and that different subtypes of CARDs may confer binding specificity, regulating the activity of various caspases, for example.

Innate immunity to bacterial pathogens relies on the specific sensing of pathogen-associated molecular patterns (PAMPs) by pattern-recognition molecules (PRMs). In mammals, Toll-like receptors (TLRs) represent the most extensively studied class of PRMs, which have been shown to sense various PAMPs, such as lipopolysaccharide (LPS), peptidoglycan (PGN), lipoproteins, double-stranded RNA and CpG DNA (S. Akira et al., Nat. Immunol., 2, 675, 2001; R. Medzhitov, Nat. Rev. Immunol., 1, 135, 2001). While TLRs are mainly expressed at the plasma membrane, it has been recently proposed that the Nod molecules, a family of intracellular proteins including Nod1/CARD4 and Nod2/CARD15, could represent a new group of PRMs that sense bacterial products within the cytoplasmic compartment, thus allowing to detect the presence of intracellular invasive bacteria (N. Inohara et al., J. Biol. Chem. 274, 14560, 1999; J. Bertin et al., J. Biol. Chem., 274, 12955, 1999; N. Inohara et al., J. Biol. Chem., 276, 2551, 2001; S. E. Girardin et al., EMBO Rep., 2, 736, 2001; Y. Ogura et al., J. Biol. Chem., 276, 4812, 2001; Y. Ogura et al., Nature, 411, 603, 2001; J. P. Hugot et al., Nature, 411, 599, 2001).

The partial sequences (cDNA and protein) of Nod1, also named CARD4 for Caspase Recruitment Domain, have been disclosed in patent application Ser. No. 09/019,942, filed Feb. 6, 1998, and now granted as U.S. Pat. No. 6,033,855. Furthermore, Bertin et al. (1999) disclosed the entire amino acid sequence of CARD4 and one of its functions, already mentioned in the above-patent: CARD4 coordinates NF-κB and apoptotic signaling pathway. Girardin et al. (2001) disclosed that CARD4/Nod1 mediates NF-κB activation by invasive *Shigella flexneri*. In this article, the interaction between *S. flexneri* LPS and CARD4 is especially studied.

Stimulation of Nod1/CARD-4 activity is desirable in situations in which CARD-4 is abnormally downregulated and/or in which increased CARD-4 activity is likely to have a beneficial effect. Conversely, inhibition of CARD-4 activity is desirable in situations in which CARD-4 is abnormally upregulated, e.g., in myocardial infarction, and/or in which decreased CARD-4 activity is likely to have a beneficial effect. Since CARD-4 may be involved in the processing of cytokines, inhibiting the activity or expression of CARD-4 may be beneficial in patients that have aberrant inflammation.

It has recently been shown that Nod1 senses the presence of the Gram-negative pathogen, *Shigella flexneri*, within the cytoplasmic compartment of epithelial cells (S. E. Girardin et al., 2001), and it was hypothesized that the detected PAMP was LPS since commercial preparations of LPS were shown to activate Nod1 (N. Inohara et al., J. Biol. Chem., 276, 2551, 2001). However, as these LPS often contain bacterial cell wall contaminants, there is a need in the art for more detail on whether a particular molecular motif or motifs are actually detected by Nod1 and modulate Nod1 activity.

SUMMARY OF THE INVENTION

This invention aids in fulfilling this need in the art. In one embodiment, this invention provides a method for modulating Nod1 activity, wherein the method comprises:
(a) expressing a functional Nod1 in a eukaryotic cell; and
(b) bringing said cell into contact with a molecule related to MTP.

This invention also provides such a method, wherein Nod1 activity is increased and the molecule related to MTP is a molecule having an agonist activity compared to the activity of MTP on Nod1. In one embodiment the molecule related to MTP is the tripeptide L-Ala-D-Glu-mesoDap, a biologically active derivative thereof, or a peptidomimetic thereof.

In another embodiment, the molecule related to MTP is MTP, a biological derivative thereof, or a peptidomimetic thereof. Nod1 activity can be decreased and the molecule related to MTP is a molecule which activity is antagonist to MTP on Nod1.

Further, this invention provides a method for modulating inflammation and/or apoptosis in a mammal, wherein the method comprises administering a molecule related to MTP to the mammal. In one embodiment, inflammation and/or apoptosis is increased and the molecule related to MTP is a molecule which activity is agonist to the activity of MTP on Nod1, and in another embodiment inflammation and/or apoptosis is decreased and the molecule related to MTP is a molecule which activity is antagonist to the activity of MTP on Nod1.

In addition, this invention provides a composition, which comprises a biologically acceptable carrier and a biologically effective amount of a molecule related to MTP.

This invention also provides a compound, which is a tripeptide having the structure L-Ala-D-Glu-mesoDAP, or a biological derivative or a peptidomimetic thereof.

Still further, this invention provides a compound for increasing in vivo inflammation and/or apoptosis or useful as an adjuvant agent in eukaryotes, wherein the compound is a tripeptide having the structure L-Ala-D-Glu-mesoDAP, or a biological derivative or a peptidomimetic thereof, and wherein, when the compound is used as an adjuvant agent, the amino acid Ala of said tripeptide is not linked to a N-acylmuramic acid. The compound is suitable for use as an adjuvant.

A composition of the invention comprises an antigen and a biologically effective amount of a molecule of the invention. The composition can comprise an immunogen and a biologically effective amount of the molecule.

This invention provides a method for enhancing the immune response of a host, which comprises administering to a host an antigen or a product of interest capable of inducing an immune response by the host, associated with a composition, which contains a biologically acceptable carrier and the compound of the invention in an amount sufficient to enhance the immune response. The method can comprise administering an amount effective to promote an immune response of the composition comprising the antigen and molecule of the invention.

In addition, this invention provides an immunogenic composition against a bacterial pathogen containing an antigen of interest and the molecule in an amount effective to enhance the effect of the immunogenic composition.

Also, this invention provides a method of vaccination of a human or an animal host, which comprises administering to that host an amount effective, for vaccination, of the immunogenic composition of the invention. Preferably, the host is human or a warm-blood animal.

Further, this invention provides a method for detecting the dysfunction of a molecule of the inflammatory and/or apoptosis pathway in which Nod1 is involved, wherein the method comprises:
(a) providing a cell in which the dysfunction of a molecule of the inflammatory and/or apoptosis pathway in which Nod1 is involved is suspected,
(b) bringing the cell into contact with MTP or an agonist thereof, and
(c) evaluating NF-κB activation or IL-8 production;
wherein an altered activation of NF-κB or an altered production of IL-8 is indicative of a dysfunction of a molecule of the inflammatory and/or apoptosis pathway in which Nod1 is involved.

A method of the invention for screening a molecule, which is capable of modulating an inflammatory and/or apoptotic response obtained after direct or indirect interaction between Nod1 and MTP, comprises:
(a) providing a cell expressing a functional Nod1;
(b) bringing the cell into contact with the molecule to be tested;
(c) measuring the activation of NF-κB and/or the production of IL-8; and optionally
(d) comparing the result of step (c) with a result obtained in absence of the molecule to be tested;
wherein the altered NF-κB activation and/or IL-8 production compared to NF-κB activation and/or IL-8 production in the absence of the molecule to be tested is indicative of the capability of the tested molecule to modulate an inflammatory response resulting from the infection of a mammal by a Gram-negative bacteria. This invention includes a molecule identified by the screening process.

Also, this invention provides a method for the modulation of inflammation and/or apoptosis in a mammal, comprising administering a molecule identified by the screening process to the mammal.

Further, this invention provides a peptidic complex containing Nod1 and MTP or a derivative or a peptidomimetic thereof, and a composition of the invention for preventing or treating a Gram-negative bacteria infection.

The present invention also provides a method for the detection of peptidoglycan from a Gram-negative bacteria in a sample, wherein the method comprises:
a) providing a sample in which peptidoglycan is to be detected;
b) bringing said sample into contact with Nod1 protein;
c) detecting an interaction between MTP and Nod1;
wherein an interaction between MTP and Nod1 is indicative of the presence of peptidoglycan from Gram-negative bacteria in the sample.

In a particular embodiment, the invention provides a method for the detection of peptidoglycan in a sample, and optionally determining the Gram-negative or Gram-positive bacterial origin of said peptidoglycan, wherein the method comprises:
a) providing a sample in which peptidoglycan is to be detected;
b) bringing said sample into contact with Nod1 protein and with Nod2 protein;
c) detecting an interaction between MTP and MDP and at least one of the two Nod proteins; and optionally
d) distinguishing between the interaction with Nod1 from the interaction with Nod2;

wherein an interaction with at least one of two Nod proteins in c) is indicative of the presence of peptidoglycan I the sample and wherein an interaction with only Nod2 in d) is indicative of a peptidoglycan of Gram-positive bacteria origin in the same while an interaction with Nod1 and Nod2 is indicative of a peptidoglycan of Gram-negative origin in the sample.

Accordingly, the above methods allow detecting the presence of bacteria in a sample, and optionally determining whether said bacteria are from Gram-negative or Gram-positive origin.

Finally, the invention provides a method for screening a molecule that modulates interaction between Gram-negative bacteria peptidoglycan and Nod1, wherein said method comprises:

a) providing MTP;

b) bringing said MTP into contact with Nod1 protein in the presence and in the absence of the tested molecule;

c) evaluating the interaction between MTP and Nod1 in the presence and in the absence of the tested molecule;

wherein a modulation of the interaction between MTP and Nod1 in the presence of the tested molecule indicates that said molecule modulates said interaction.

BRIEF SUMMARY OF THE DRAWINGS

This invention will be described in greater detail with reference to the drawings in which:

FIGS. 5A-5C are a schematic representation of the muropeptides derived from PGNs of various bacteria.

FIG. 5A: muropeptide found in Gram-negative bacteria, containing a mesoDAP amino acid.

FIG. 5B: muropeptide found in some Gram-positive bacteria such as *B. subtilis*. Instead of the mesoDAP, an amidated-DAP is found.

FIG. 5C: muropeptide found in most Gram-positive bacteria, containing a L-lysine as third amino acid.

Note that the only difference between these muropeptides take place at the third amino acid position.

Figure 6A:
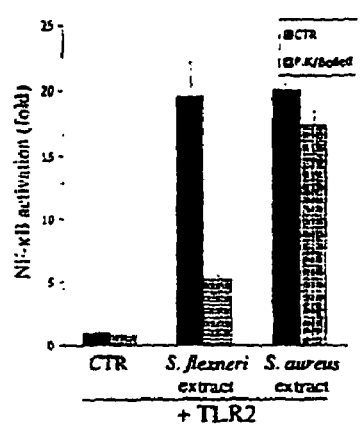
Figure 6B:
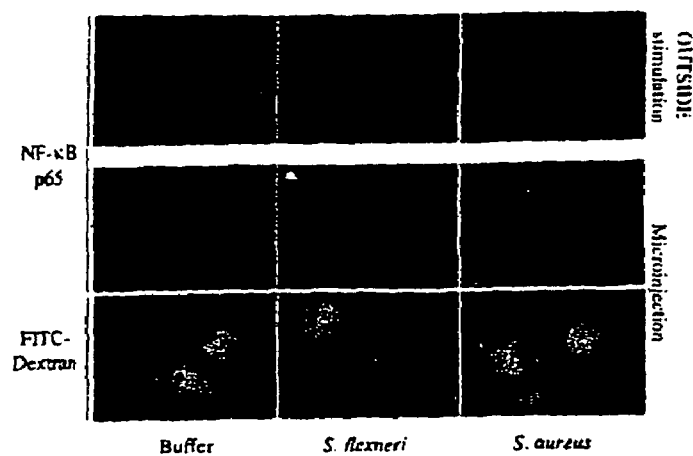

FIGS. 6A-6B depict the results of the relative PGN content of bacterial extracts prepared. NF-κB activation was assessed by translocation of the NF-κB p65 subunit from the cytosol to the nucleus in microinjected cells.

Figures 3A, 3B, 3C, 3D, 3E:
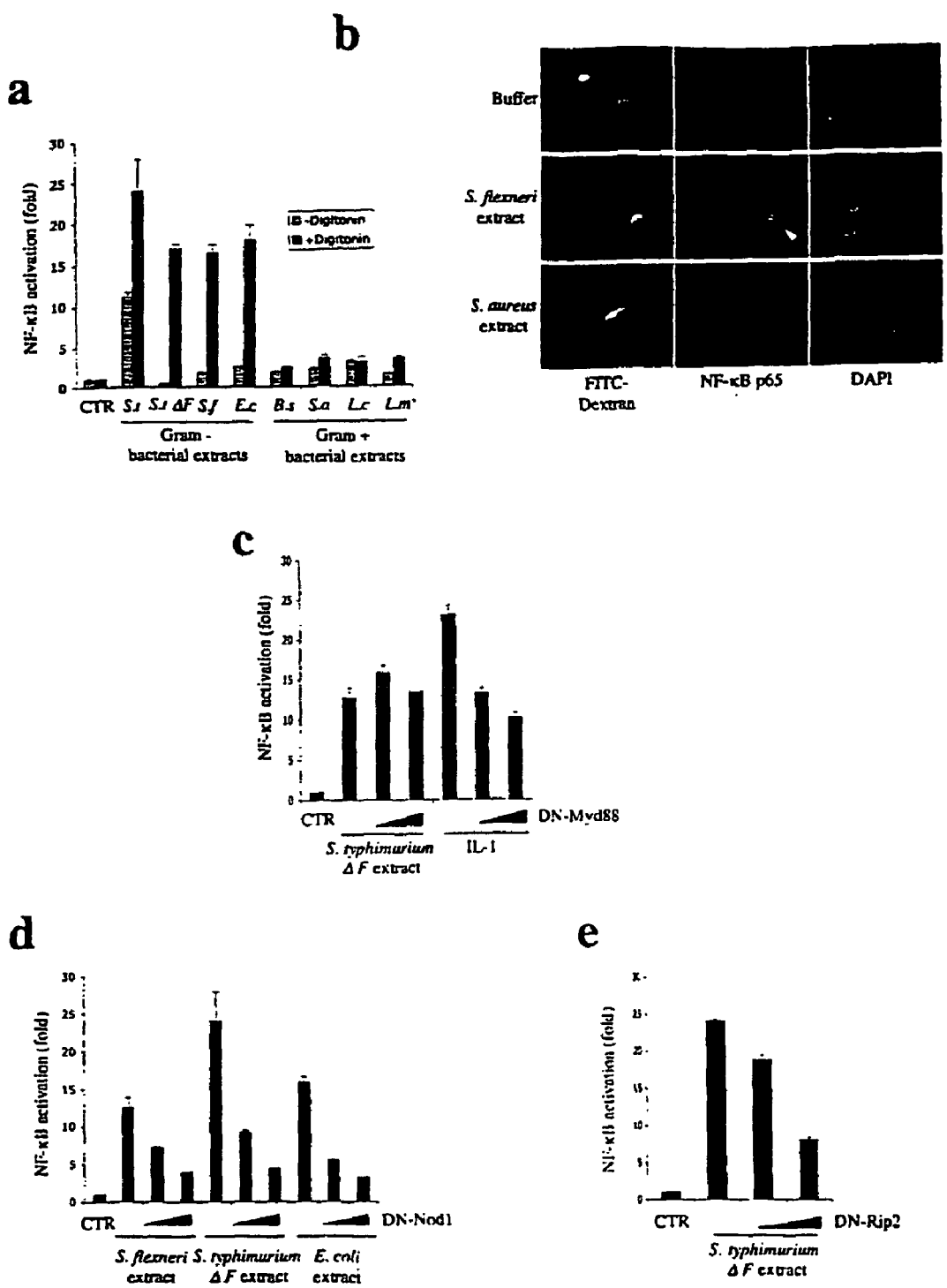
FIGS. 3A-3E show the results of intracellular detection of Gram-negative, but not Gram-positive bacterial products, in epithelial cells through Nod1/Rip2, but not MyD88.

FIG. 6A: we aimed to determine the relative PGN content of the bacterial extracts prepared. To this end, TLR2-overexpressing HEK293 cells were stimulated by extracellular addition of bacterial extracts treated or not with proteinase K and boiling, which affects lipoprotein activity. In this way, we could analyze the relative contribution of bacterial lipoprotein versus PGN towards TLR2 stimulation. We observed that bacterial extracts from Gram-negative bacteria displayed much less PGN activity than extracts from Gram-positive bacteria cultured to the same optical density (FIG. 3A). This finding is not surprising since it is well known that Gram-negative bacteria contain less PGN than Gram-positive bacteria and also recycle PGN to a higher extend during growth.

FIG. 6B: bacterial extracts from *S. flexneri* and *S. aureus* were micro-injected together with FITC-Dextran into Caco-2 epithelial cells. After 30 minutes, the cells were fixed and analyzed for NF-$_κ$B activation by immunofluorescence. NF-$_κ$B activation was assessed by translocation of the NF-$_κ$B p65 subunit from the cytosol to the nucleus in microinjected cells. Activation of NF-$_κ$B was observed only in Caco-2 cells microinjected with bacterial extracts from Gram-negative bacteria. We also observed the lack of NF-$_κ$B activation in Caco-2 cells following extracellular addition of bacterial extracts, suggesting that these cells do not display a functional endogenous TLR sensing system.

Figure 7A:
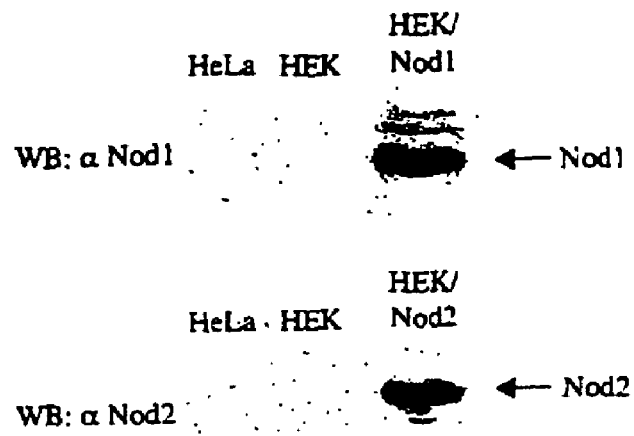
Figure 7B:
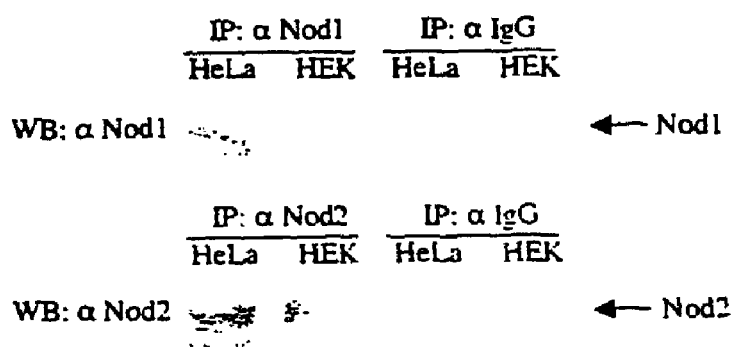

FIGS. 7A-7B show that Nod1 and Nod2 are expressed in HeLa and HEK 293 epithelial cells. Nod1 and Nod2 are expressed in HeLa and HEK 293 epithelial cells.

FIG. 7A: protein extracts ($2.10^4$ cells/lane) from HeLa and HEK 293 cells were directly analyzed by western blot for endogenous expression of Nod1 and Nod2, using specific polyclonal antibodies raised against human forms of Nod1 and Nod2, respectively (see Methods Section). Note that endogenous expressions of Nod1 and Nod2 remained undetectable using this technique, and therefore protein extracts from HEK 293 transiently transfected with expression vectors for Nod1 (HEK/Nod1) and Nod2 (HEK/Nod2) were analyzed in parallel in order to show the specificity of the antibodies.

FIG. 7B: protein extracts ($10^7$ cells/lane) from HeLa and HEK 293 cells were immunoprecipitated using Nod1, Nod2 or control IgG antibodies prior to analysis by western blot as indicated. This immunoprecipitation technique was required to detect the presence of the endogenous forms of Nod1 and Nod2, since it allowed for the concentration of Nod1 and Nod2 present in cell extracts by ~500 fold.

FIGS. 8A-8D show the peptidoglycan structures required for the detection by Nod1.

Figure 8A:
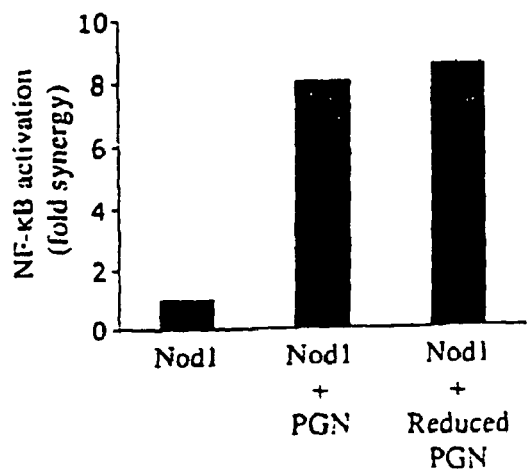

FIG. 8A shows that detection of peptidoglycan by Nod1 does not require a cyclic sugar moiety.

Figure 8B:
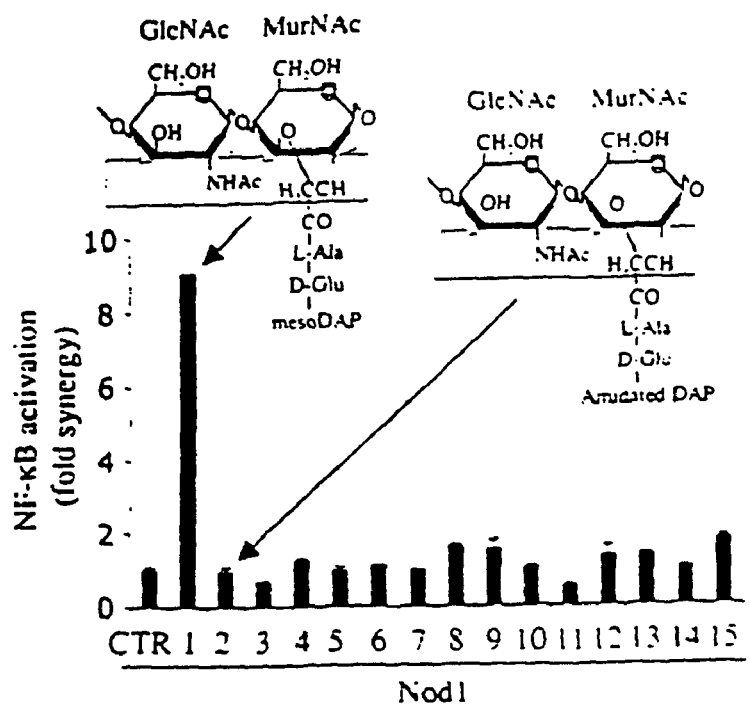

FIG. 8B shows that Nod1 detects meso-DAP-containing GM-tripeptide, but not amidated-DAP-containing GM-tripeptide.

Figure 8C:
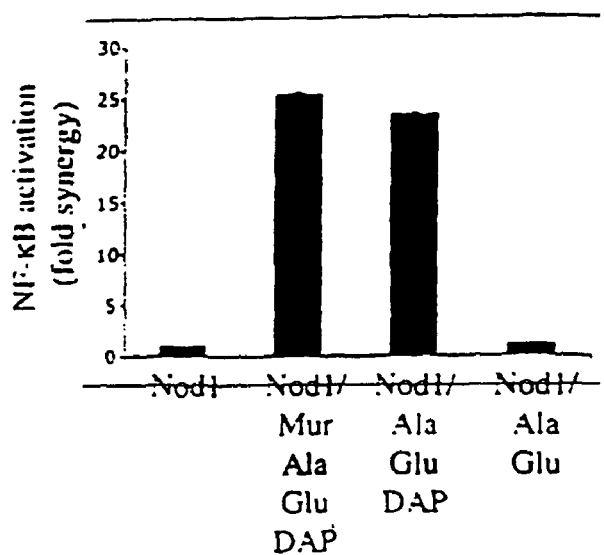

FIG. 8C shows that Nod1 detects TriDAP.

Figure 8D:
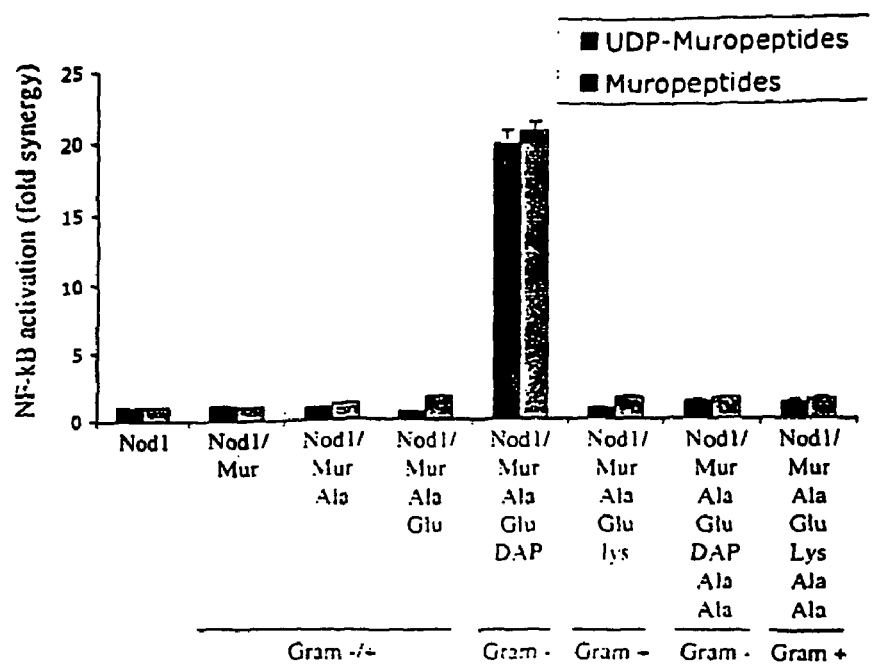

FIG. 8D shows that Nod1 detects UDP-MurTriDAP and MurTriDAP.

DETAILED DESCRIPTION OF THE INVENTION

As used herein, MTP means muramyl tripeptide from the peptidoglycan of the cell wall of a Gram-negative bacteria, that is GlcNAc-MurNAc-L-Ala-D-Glu-mesoDAP or meso-DAP containing GM-tripeptide.

As used herein, the terms "a molecule related to MTP" means a molecule or a compound having activity that is agonist or antagonist to the activity of MTP on Nod1. Molecules related to MTP comprise, but are not limited to, MTP, the tripeptide L-Ala-D-Glu-mesoDAP, biologically active derivatives of MTP, such as, for example, the peptide fraction of MTP that is the three amino acids without the sugar moieties, MTP without GlcNAc, MTP with non-cyclized sugar, peptidomimetics, and molecules having activity that is antagonist to the one of MTP on Nod1.

The activity of the molecule related to MTP can be evaluated by the tests disclosed in the Examples: Evaluation of NF-κB activation or of IL-8 production for instance. A molecule having activity as agonist to MTP activity on Nod 1 increases NF-κB activation or IL-8 production. A molecule having activity as antagonist to MTP activity on Nod 1 decreases NF-κB activation or IL-8 production.

As used herein, the terms "biologically active derivatives" refers to function-conservative variants, homologous proteins or peptides and peptidomimetics, as well as a hormone, an antibody or a synthetic compound, (i.e., either a peptidic or non-peptidic molecule) that preferably retains the binding specificity and/or physiological activity of the parent peptide, as defined herein.

Also part of the invention are preferred peptidomimetics retaining the binding specificity and/or physiological activity of the parent peptide, as described herein and that they are positive in a test of activity as disclosed for testing one.

As used herein, "peptidomimetic" is an organic molecule that mimics some properties of peptides, preferably their binding specificity and/or physiological activity. Preferred peptidomimetics are obtained by structural modification of peptides according to the invention, preferably using unnatural amino acids, D. amino acid instead of L. amino acid, conformational restraints, isosteric replacement, cyclization, or other modifications. Other preferred modifications include without limitation, those in which one or more amide bond is replaced by a non-amide bond, and/or one or more amino acid side chain is replaced by a different chemical moiety, or one or more of the N-terminus, the C-terminus or one or more side chain is protected by a protecting group, and/or double bonds and/or cyclization and/or stereospecificity is introduced into the amino acid chain to increase rigidity and/or binding affinity.

Modifications can also be made for preparing molecules having activity that is antagonist to the one of Nod1.

While the role of Toll-like receptors in extracellular bacterial sensing has been investigated intensively, intracellular detection of bacteria through Nod molecules remains largely uncharacterized. This invention shows that Nod1 detects specifically a unique diaminopimelate-containing GlcNAc-MurNAc tripeptide motif found in Gram-negative bacterial peptidoglycan, resulting in activation of the NF-κB pathway. Moreover, this invention shows, in epithelial cells which represent the first line of defense against invasive pathogens, that Nod1 is indispensable for intracellular Gram-negative bacterial sensing. Nod1 represents so far the first example of a pathogen-recognition molecule that specifically senses Gram-negative bacterial peptidoglycan.

Furthermore, this invention shows that Nod1 specifically senses MTP and more specially the peptide moiety of the GlcNAc-MurNAc tripeptide.

In the present invention, the inventors show that LPS was a contaminant in the previous studies and that Nod1 detects specifically a unique motif found in the peptidoglycan of Gram-negative bacteria: a muramyl tripeptide carrying at its third position a diaminopimelic amino acid.

Numerous publications are directed to MDP (muramyl dipeptide) and its adjuvant property. There are also publications about the adjuvant properties of MTP (muramyl tripeptide), which are generally directed to MTP-PE that is to muramyl tripeptide phosphatidylethanolamine. A first patent, FR 2 160 326, filed Nov. 19, 1971, concerns a process for preparing a soluble agent having an adjuvant activity, wherein the soluble agent is extracted from mycobacteria or Nocardia cell walls. FR 2 248 025, filed on Oct. 23, 1973, and is an addition to FR 2 160 326 and discloses the discovery that the adjuvant activity of this soluble agent comes from soluble fragments of peptidoglycans of the cell wall and concerns specific muramyl peptides. The U.S. equivalent is U.S. Pat. No. 4,186,194. The subject invention was made as follows.

The tripeptide according to the U.S. Pat. No. 4,186,194 contains always sugar moieties.

Figures 1A, 1B, 1C, 1D:
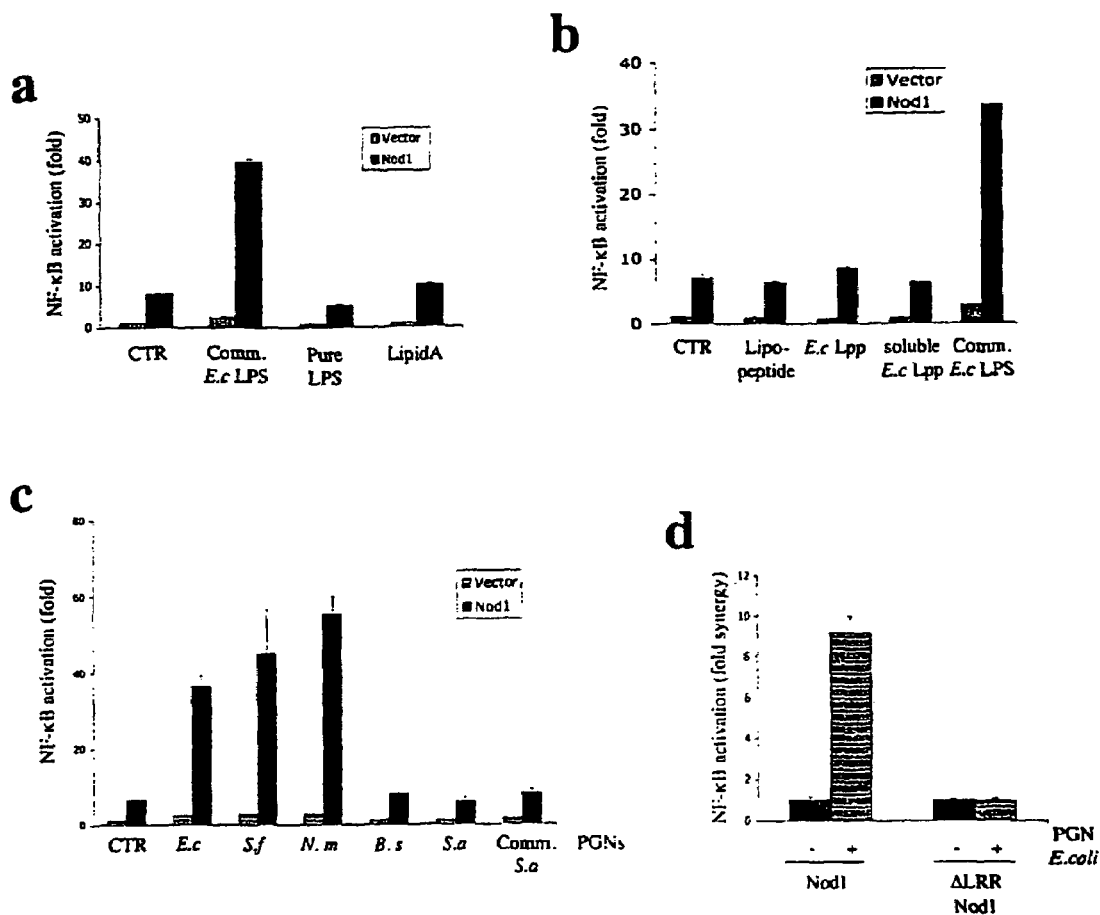
FIGS. 1A-1D show that the Nod1 pathway is stimulated by commercial LPS and Gram-negative bacterial PGNs.

Addition of a commercial preparation of *Escherichia coli* LPS (10 μg) to Nod1-overexpressing HEK293 cells could potentiate by ~5 fold the level of Nod1-dependent NF-κB activation (FIG. 1A). On the contrary, highly purified *E. coli* LPS (10 μg) or lipid A (10 μg) could not stimulate the Nod1 pathway (FIG. 1A), although they could efficiently activate macrophages. These findings show that a contaminant present in commercial LPS preparations is likely responsible for Nod1 activation. Therefore, one aim was to identify the nature of this contaminant. Lipoproteins have been recently identified as the major contaminants of LPS preparations responsible for TLR2 signaling following stimulation with commercial *E. coli* LPS (K. Lee et al., P. S. Tobias, J. Immunol., 168, 4012, 2002). However, it was not possible to stimulate the Nod1 pathway by addition of either synthetic lipopeptide or Lpp, the most abundant lipoprotein in *E. coli* (FIG. 1B). Moreover, boiling or proteinase K treatment of the commercial LPS was not sufficient to abolish Nod1 signaling.

Figure 4:
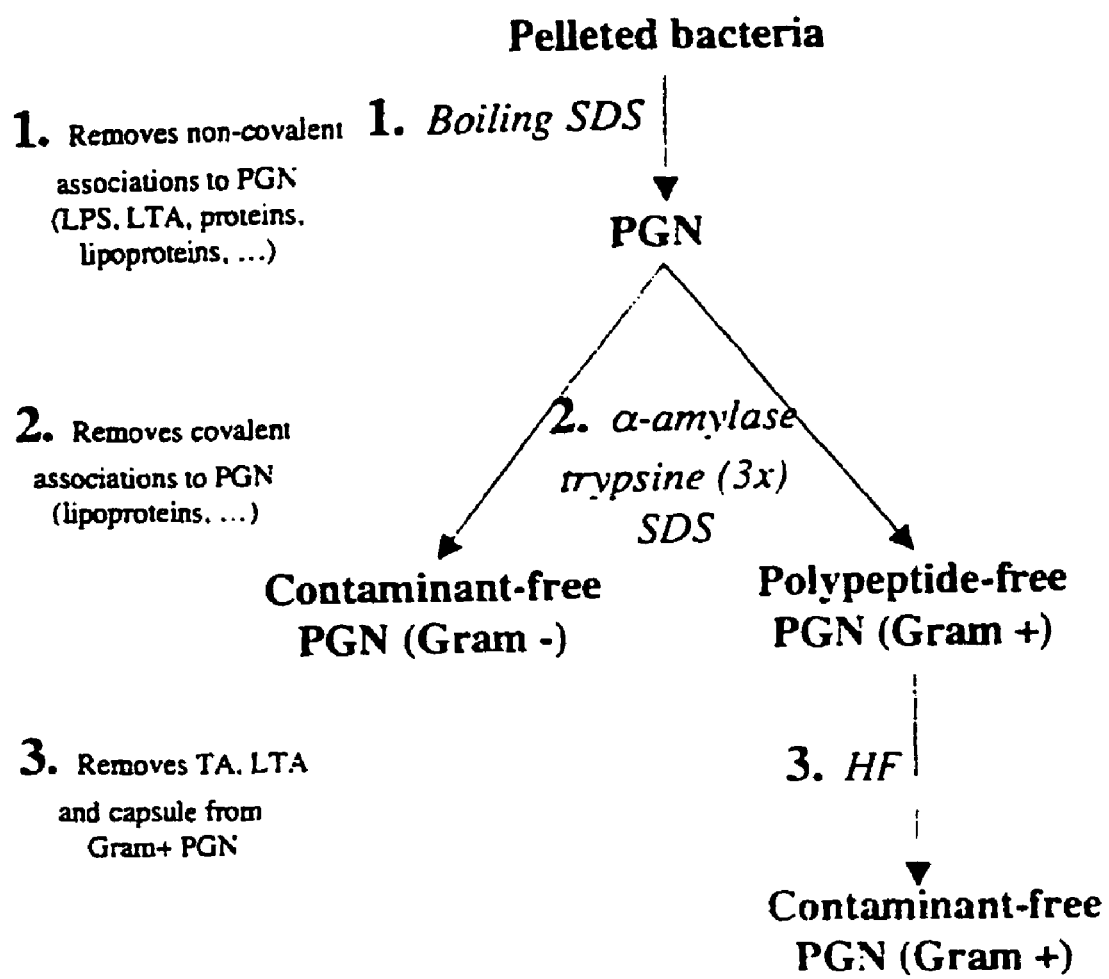
FIG. 4 depicts the experimental procedure followed to prepare highly purified PGNs from Gram-negative or Gram-positive bacteria.

The next aim was to address the potential role of PGN in stimulating the Nod1 signaling pathway. Therefore, PGNs from *E. coli, S. flexneri, Neisseria meningitidis, Bacillus subtilis* and *Staphylococcus aureus* were purified according to experimental procedures specifically designed for Gram-positive or Gram-negative bacteria (B. L. de Jonge et al., J. Biol. Chem., 267, 11248, 1992; B. Glauner, Anal. Biochem., 172, 451, 1988). The harsh purification steps used to purify these PGNs eliminate the possible contaminants (FIG. 4). Strikingly, it was observed that PGN preparations from Gram-negative bacteria could stimulate the Nod1 pathway, while the two Gram-positive PGN preparations tested here could not (FIG. 1C). Moreover, by using a mutant form of Nod1 that lacks the C-terminal leucine-rich repeats (LRRs), it was observed that Nod1 LRRs play a critical role in the sensing of Gram-negative PGN (FIG. 1D). Therefore, these results strongly suggested that Nod1 is an intracellular PRM that specifically senses Gram-negative PGN through the LRR domain.

Figures 2A, 2B, 2C, 2D, 2E, 2F:
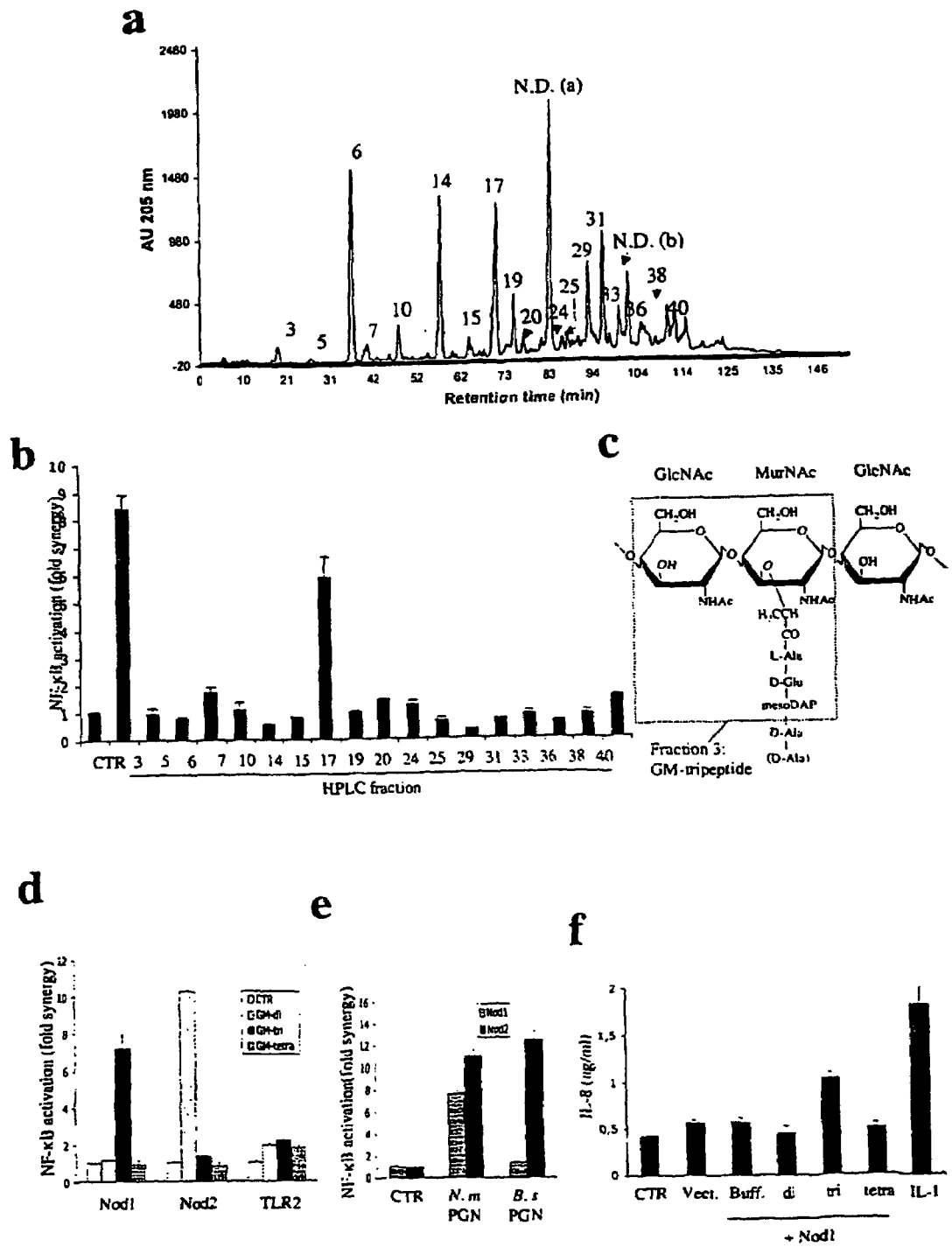
FIGS. 2A-2F are a characterization of the PGN motif detected by Nod1.

In order to identify the minimal PGN motif detected by Nod1, muropeptides from *N. meningitidis* were analyzed by reverse-phase HPLC after PGN digestion with a muramidase. Indeed, the major PGN fragments naturally released by Gram-negative bacteria are muropeptides (J.-H. Höltje, Microbiol. Mol., Biol. Rev., 62, 181, 1988; N. T. Blackburn et al., J. Mol. Evol., 52, 78, 2001). This analysis allowed for the separation of muropeptides according to the number of amino acids of the peptidic chain linked to the amino sugars, the degree of polymerization of the peptidic chain or natural modifications such as O-acetylation or dehydration of the amino sugars (FIG. 2A).

Individual muropeptides were collected and tested for their ability to activate the Nod1 pathway. Surprisingly, only two fractions (3 and 17) contained muropeptides able to activate Nod1 (FIG. 2B). Mass spectroscopy analysis revealed that fraction 3 is a muropeptide with a molecular mass of 893 m/z and the active molecule in fraction 17 is a muropeptide of 873 m/z. The 893 m/z molecule is consistent with a reduced muropeptide Nacetylglucosamine (GlcNAc or "G") β-1,4 linked to N-acetylmuramic acid (MurNAc or "M"), substituted with a tripeptide group (FIG. 2C), while the 873 m/z molecule corresponds to the same muropeptide naturally dehydrated on the MurNAc moiety (anhydro-MurNAc). The tripeptide group substituted on the MurNAc, L-Ala-D-Glu-mesoDAP (where Ala is Alanine, Glu is Glutamine and DAP is diaminopimelate), is therefore the same in the fractions 3 and 17. HPLC analyses and biological assays were carried out on muropeptides isolated from *S. flexneri* with similar findings.

To gain more insight into the molecular pattern sensed by Nod1, a comparison was made of the activation of the Nod1 pathway by GM-dipeptide, GM-tripeptide and GM-tetrapeptide. Equivalent amounts (10 ng) of GM-dipeptide, GM-tripeptide (from fraction 3) and GM-tetrapeptide (fraction 6)

were tested for their ability to activate the Nod1 pathway. It was observed that Nod1 specifically detects GM-tripeptide but not GM-dipeptide nor GM-tetrapeptide (FIG. 2D). Since Nod1 is closely related to Nod2, these PGN products were also tested for Nod2 detection. Previous findings and those of Inohara et al. had shown that Nod2 recognizes M-dipeptide (S. E. Girardin et al., J. Biol. Chem., 278, 8869, 2003; N. Inohara et al., J. Biol. Chem., 278, 5509, 2003). Strikingly, it was discovered that Nod2 detects GM-dipeptide in addition to M-dipeptide but not GM-tripeptide or GM-tetrapeptide (FIG. 2D), suggesting that these two Nod molecules both sense PGN but require distinct molecular motifs to achieve detection. It was also observed that TLR2 could not detect any of the muropeptides tested (FIG. 2D).

Figure 5C:
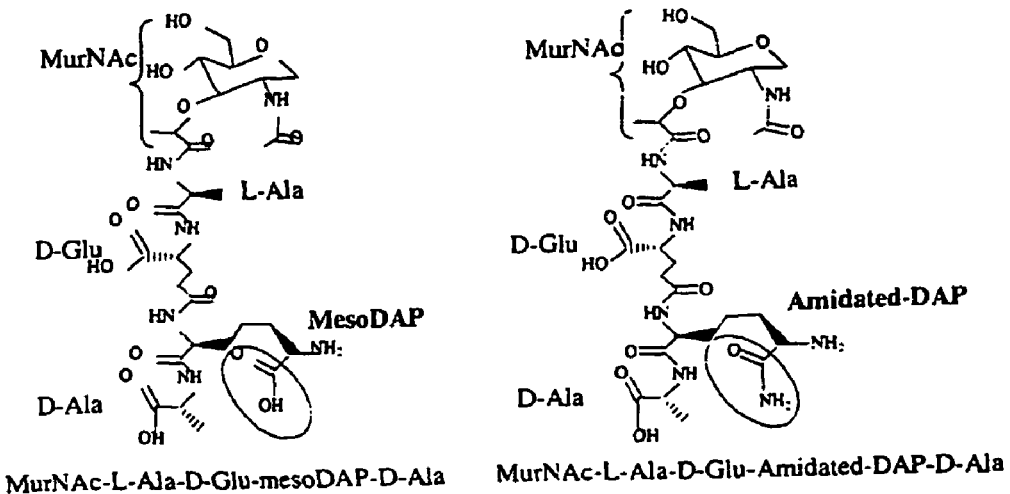
Figure 5C:
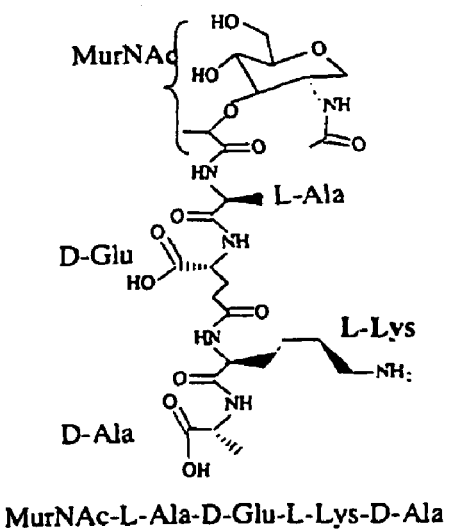

The PGN motif sensed by Nod2, GM-dipeptide, is found in all bacteria, suggesting that Nod2 is a general sensor of PGN degradation products (S. E. Girardin et al., 2003; N. Inohara et al., 2003). In contrast, the additional requirement of mesoDAP for Nod1 sensing explains why Nod1 detects only those PGNs purified from Gram-negative bacteria (see FIG. 1C) as compared to the Gram-positive PGNs tested. Indeed, while S. aureus PGN contains lysine instead of mesoDAP, B. subtilis contains amidated-diaminopimelate (FIGS. 5A-5C). Furthermore, S. aureus PGN does not have any detectable amounts of GM-tripeptide (B. L. de Jonge et al., 1992). In addition, these findings also indicate that the Nod1 sensing system requires an exposed mesoDAP since the GM-tetrapeptide, which also contains mesoDAP, is not sensed by Nod1. It was next observed that Nod2, which does not require mesoDAP to achieve PGN detection, could sense both B. subtilis and N. meningitidis PGNs (FIG. 2E). In contrast, even if the B. subtilis PGN shares some structural similarities with mesoDAP containing PGNs (FIGS. 5A-5C), Nod1 does not detect B. subtilis PGN (FIG. 2E, also shown in FIG. 1C). In addition to NF-κB activation, it was found that sensing of the GM-tripeptide by Nod1 also leads to the production of the pro-inflammatory chemokine, interleukin-8 (FIG. 2F), which is one of the major cytokines produced by epithelial cells infected with Gram-negative bacteria (L. Eckmann et al., J. Biol. Chem., 275, 14084, 2000; T. Pedron et al., J. Biol. Chem., 278(36), 33878-86, 2003). Taken together, these results show that for Nod1-dependent activation of NF-κB and IL-8, the PGN structural requirements include GM linked to a tripeptide and a terminal mesoDAP amino acid in which both carboxy groups play a major role.

Next, it was of interest to determine the contribution of PGN detection by Nod1 in the context of intracellular bacterial sensing by epithelial cells. Indeed, previous studies stressed the pivotal role of these cells as the first line of defense against bacterial pathogens at mucosal surfaces. First, extracts were prepared from various Gram-negative or Gram-positive bacteria and determined the relative PGN content of these extracts (FIG. 6A). Then, these bacterial extracts were added extracellularly and showed that they were unable to activate NF-κB in HEK293 epithelial cells (FIG. 3A), confirming that these cells do not display an endogenous TLR2/4 sensing system. The only exception was Salmonella typhimurium extract; in this case NF-κB activation is likely to involve TLR5 (F. Hayashi et al., Nature, 410, 1099, 2001), since extracts from a flagellin-deficient S. typhimurium strain were unable to stimulate the NF-κB pathway (FIG. 3A). A digitonin-based permeabilization technique was then used to elicit entry of bacterial products into the cytoplasm allowing a direct comparison of the ability of bacterial products from either invasive or non-invasive bacteria to activate the NF-κB pathway. It was observed that extracts from a number of Gram-negative bacteria were able to stimulate the NF-κB pathway while those from the four Gram-positive bacteria were not (FIG. 3A). The specific activation of NF-κB by only Gram-negative extracts was confirmed in two other epithelial cell lines (HeLa and Caco-2) by microinjection of bacterial products from either S. flexneri or S. aureus, followed by detection of the NF-κB p65 subunit nuclear translocation by immunofluorescence (FIG. 3B and FIG. 6B).

Therefore, these data show that epithelial cells sense Gram-negative but not Gram-positive bacterial products when presented to the cytoplasmic compartment. These findings are consistent with the fact that the released PGN motifs from the Gram-negative bacteria tested here all contain GM-tripeptide with a terminal mesoDAP, and that released Gram-positive bacterial PGN products lack this structure. In the case of L. monocytogenes, the PGN contains mesoDAP; however, the PGN degradation products have not yet been characterized. Of interest, the major PGN hydrolase in L. monocytogenes is a N-acetylmuramoyl-L-alanyl-amidase that cleaves the bond between the PGN sugar backbone and the peptidic chains. Therefore, L. monocytogenes is unlikely to release significant amounts of muropeptides but rather free peptidic chains and amino sugars (A. M. McLaughlan et al., Microbiology, 144, 1359, 1998).

To characterize which signaling pathways are involved in intracellular sensing of Gram-negative bacterial extracts by epithelial cells, it was first demonstrated that this pathway was independent of MyD88, a key adaptor protein of the TLR/IL-1 pathway (T. Kawai et al., Immunity, 11, 115, 1999), since a dominant-negative form of MyD88 was unable to block the activation of the NF-κB pathway induced in digitonin-permeabilized cells by extracts from Gram-negative bacteria, including S. typhimurium ΔF, S. flexneri and E coli (FIG. 3C and data not shown). On the contrary, using a dominant-negative form of Nod1 (DN-Nod1), it was possible to efficiently block NF-κB activation induced in digitonin-permeabilized cells by bacterial products from S. flexneri, S. typhimurium and E. coli (FIG. 3D). Several reports have shown that Nod1 activates the NF-κB pathway through the recruitment of Rip2 (S. E. Girardin et al., 2001; N. Inohara et al., J. Biol. Chem., 275, 27823, 2000; A. I. Chin et al., Nature, 416, 190, 2002; K. Kobayashi, et al., Nature, 416, 194, 2002). Accordingly, it was observed that a dominant-negative form of Rip2 also blocks the NF-κB pathway induced in digitonin-permeabilized cells by extracts from Gram-negative bacteria (FIG. 3E).

These findings, therefore, demonstrate that Nod1 is the crucial intracellular sensor of bacterial products in epithelial cells and that induction of the Nod1-dependent pro-inflammatory pathway depends upon the ability of a bacterial pathogen, either invasive or extracellular, to translocate Gram-negative PGN to the intracellular environment.

Moreover, additional experiments were conducted on fraction of the GM-dipeptide and surprisingly it has been found that Nod1 is able to sense the tripeptide L-Ala-D-Glu-mesoDAP without the sugar moieties. Therefore, the shortest motif sensed by Nod1, which is identified is the tripeptide.

It will be understood that this invention includes antagonists and agonists of Nod1 that can inhibit or enhance, respectively, one or more of the biological activities of Nod1. Suitable antagonists include small organic or inorganic molecules (i.e., molecules with a molecular weight below about 500), large molecules (i.e., molecules with a molecular weight above about 500), antibodies, and nucleic acid molecules. Agonists of Nod1 also include combinations of small and large molecules.

Thus, the invention features (1) methods for modulating (e.g., decreasing or increasing) an activity of Nod1 by contacting a cell expressing a functional Nod1 with a compound, which activates to Nod1 in a sufficient concentration to modulate the activity of Nod1; and (2) methods of identifying a compound that modulates the activity (e.g., decrease or increase) of Nod1 by contacting the Nod1 with a test compound (e.g., polypeptides, ribonucleic acids, small molecules, large molecules, ribozymes, antisense oligonucleotides, and deoxyribonucleic acids), and detecting and comparing the level of activity of Nod1 in the presence or absence of the test compound.

Compounds that modulate the activity of Nod1 in a cell can be identified by comparing the activity of Nod1 in the presence of a selected compound with the activity of Nod1 in the absence of that compound. A difference in the level of Nod1 activity indicates that the selected compound modulates the expression of Nod1 in the cell.

Exemplary compounds that can be screened in accordance with the invention include, but are not limited to, small organic molecules that are able to gain entry into an appropriate cell and affect the activity of Nod1 protein.

Computer modeling and searching technologies permit identification of compounds, or the improvement of already identified compounds, that can modulate Nod1 activity. Having identified such a compound or composition, the active sites or regions are identified. Such active sites might typically be a binding for a natural modulator of activity. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the modulator (or ligand) is found.

Next, the three dimensional geometric structure of the active site can be determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures can be measured with a complexed modulator (ligand), natural or artificial, which can increase the accuracy of the active site structure determined.

If an incomplete or insufficiently accurate structure is determined, the methods of computer-based numerical modeling can be used to complete the structure or improve its accuracy. Any recognized modeling method can be used, including parameterized models specific to particular biopolymers, such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential Nod1 modulating compounds.

Alternatively, these methods can be used to identify improved modulating compounds from a previously identified modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modelling of drugs interactive with specific proteins, such as Rotivinen et al., Acta Pharmaceutical Fennica, 97:159 [1993]; Ripka, New Scientist 54-57 [Jun. 16, 1988]; McKinaly and Rossmann, Annu Rev Pharmacol Toxicol, 29:111 [1989]; Perry and Davies, OSAR: Quantitative Structure-Activity Relationships in Drug Design, pp. 189-193 (Alan R. Liss, Inc. 1989); Lewis and Dean, Proc. R. Soc. Lond., 236:125 [1989]; and 141 [1980]; and, with respect to a model receptor for nucleic acid components, Askew et al., J Am. Chem. Soc., 111:1082 [1989]). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds that could alter binding, one could also screen libraries of known compounds, including natural products or synthetic chemicals, and biologically active materials, including proteins, for compounds that are inhibitors or activators of Nod1 activity.

Compounds identified via assays, such as those described herein, are useful, for example, in elaborating the biological function of Nod1 and for the treatment of disorders associated with aberrant Nod1 activity or expression. Assays for testing the effectiveness of compounds identified with the above-described techniques are discussed below.

In vitro systems may be designed to identify compounds capable of interacting with Nod1 (or a domain of Nod1). Compounds identified may be useful, for example, in modulating the activity of wild type and/or mutant Nod1; may be useful in elaborating the biological function Nod1; may be utilized in screens for identifying compounds that disrupt normal Nod1 interactions; or may in themselves disrupt such interactions.

The principle of the assays used to identify compounds that activate to Nod1 involves preparing a reaction mixture of Nod1 (or a domain thereof) and the test compound under conditions and for a time sufficient to allow the two components to interact and activate, thus forming a complex which can be removed and/or detected in the reaction mixture. The Nod1 species used can vary depending upon the goal of the screening assay. In some situations it is preferable to employ a peptide corresponding to a domain of Nod1 fused to a heterologous protein or polypeptide that affords advantages in the assay system (e.g., labeling, isolation of the resulting complex, etc.) can be utilized.

Cell-based assays can be used to identify compounds that interact with Nod1. To this end, cell lines that express Nod1, or cell lines that have been genetically engineered to express Nod1 can be used.

In order to test a compound for inhibitory activity, the reaction mixture is prepared in the presence and absence of the test compound. The test compound can be initially included in the reaction mixture, or can be added at a time subsequent to the introduction of the Nod1 moiety. Control reaction mixtures are incubated without the test compound or with a non-active control compound. The formation of any complexes between the Nod1 moiety and the binding partner is then detected. The formation of a complex in the control reaction, but not in the reaction mixture containing the test compound, indicates that the compound interferes with the interaction of Nod1 and the interactive binding partner. Additionally, complex formation within reaction mixtures containing the test compound and normal Nod1 protein can also be compared to complex formation within reaction mixtures containing the test compound and a mutant Nod1. This comparison may be important in those cases wherein it is desirable to identify compounds that disrupt interactions of mutant but not normal Nod1.

Other methods for identifying compounds capable modulating with Nod1 are disclosed in the Examples.

The invention encompasses methods of diagnosing and treating patients who are suffering from a disorder associated with an abnormal level or rate (undesirably high or undesirably low) of apoptotic cell death, abnormal activity of the Fas/APO-1 receptor complex, abnormal activity of the TNF receptor complex, abnormal activity of a caspase or inflammation of infectious or non-infectious origin by administering a compound that modulates the activity of Nod1. Examples of such compounds include small molecules and large molecules. It will be understood that this invention can be employed to treat a variety of disorders, such as the following.

Certain disorders are associated with an increased number of surviving cells, which are produced and continue to survive or proliferate when apoptosis is inhibited. These disorders include cancer (particularly follicular lymphomas, carcinomas associated with mutations in p53, and hormone-dependent tumors such as breast cancer, prostate cancer, and ovarian cancer), autoimmune disorders (such as systemic lupus erythematosis, immune-mediated glomerulonephritis), and viral infections (such as those caused by herpesviruses, poxviruses, and adenoviruses).

Failure to remove autoimmune cells that arise during development or that develop as a result of somatic mutation during an immune response can result in autoimmune disease. One of the molecules that play a critical role in regulating cell death in lymphocytes is the cell surface receptor for Fas.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses.

Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Certain inflammatory disorders, both of infectious and non-infectious in origin, could be treated by administering compounds that modulate Nod1 activity. Pathology of inflammatory disorders is associated with inflammation-mediated destruction of the tissue. Inflammatory diseases of non-infectious origin include, but are not limited to, allergy, asthma, psoriasis, rheumatoid arthritis, ankylosing spondylitis, autoimmune diseases (such as systemic lupus erythematosis and glomerulonephritis), and certain cancers. Infectious inflammatory diseases include such infections as those causing gastroenteritis (*Shigella* spp, *Samonella enteritidis, Campylobacter* spp., the different strains of diarrheagenic *Escherichia coli*), gastritis, gastric ulceration, and cancer (*Helicobacter pylori*), vaginitis (*Chlamydia trachomatis*,) and respiratory diseases (*Pseudomonas aeruginosa, Mycobacteria*, etc.).

Patients who have a disorder mediated by abnormal Nod1 activity can be treated by administration of a compound that alters activity of Nod1. Accordingly, the invention features methods for treating a patient having a disorder associated with the aberrant activity of Nod1 by administering a therapeutically effective amount of a compound (e.g., polypeptide, ribonucleic acid, small molecule, large molecule, ribozyme, antisense oligonucleotide or deoxyribonucleic acid) that decreases or increases the activity of Nod1. Accordingly, the invention features methods for modulating apoptosis by modulating the expression or activity of a gene encoding Nod1.

Agents or modulators, which have a stimulatory or inhibitory effect on Nod1 activity can be administered to individuals for prophylactic or therapeutic treatment of disorders associated with aberrant Nod1 activity. The individual's response to a foreign compound or drug permits the selection of effective agents, and can further be used to determine appropriate dosages and therapeutic regimens. Accordingly, the activity of Nod1 can be determined and used to select an appropriate agent for therapeutic or prophylactic treatment of the individual.

The invention encompasses methods for the detection of peptidoglycan (through MTP) from Gram-negative bacteria in a sample. These methods use the specific interaction between Gram-negative MTP and Nod1 to detect peptidoglycan from Gram-negative bacteria and then Gram-negative bacteria in a sample.

In a preferred embodiment, the present invention is directed to a method for the detection of peptidoglycan from a Gram-negative bacteria in a sample, wherein the method comprises:
 a) providing a sample in which peptidoglycan is to be detected;
 b) bringing said sample into contact with Nod1 protein;
 c) detecting an interaction between MTP and Nod1;

wherein an interaction between MTP and Nod1 is indicative of the presence of peptidoglycan from Gram-negative bacteria in the sample.

Detection of an interaction between Gram-negative MTP and Nod1 can be done by measuring NK-κB activation in a cell as disclosed in the Examples, for instance.

On the other hand, Nod1 auto-oligomerizes after infection (N. Inohara et al., 2001) is based on this characteristic, one can detect Nod1/Gram-negative MTP interaction by the detection of Nod1 oligomerization. For example, detection of Nod1 oligomerization can be performed by means of coupling of Nod1 with a probe. More particularly, the method of the invention can be performed in an acellular system and the oligomerization of Nod1 can be monitored by a physiochemical reaction. In a particular embodiment, oligomerization of Nod1 can be detected by means of FRET (fluorescence resonance energy transfer) well known by one skilled in the art, which generates a detectable bioluminescent signal.

Nod2 detects either Gram-negative or Gram-positive peptidoglycan (S. E. Girardin et al., 2003; N. Inohara et al., 2003). Thus, the methods of the invention can use Nod1 and Nod2 proteins to detect bacterial peptidoglycan, and then the presence of bacteria, in a sample and optionally to determine whether bacteria in said sample are of Gram-negative or Gram-positive origin.

In a preferred embodiment the invention encompasses a method for the detection of peptidoglycan in a sample and optionally determining the Gram-negative or Gram-positive bacteria origin of said peptidoglycan, wherein the method comprises:
 a) providing a sample in which peptidoglycan is to be detected;
 b) bringing said sample into contact with Nod1 protein and with Nod2 protein;
 c) detecting an interaction between MTP and MDP and at least one of the two Nod proteins, and optionally;
 d) distinguishing between the interaction with Nod1 from the interaction with Nod2;

wherein an interaction with at least one of the two Nod proteins in c) is indicative of the presence of peptidoglycan in the sample and wherein an interaction with only Nod2 in d) is indicative of a peptidoglycan of Gram-positive bacteria origin in the sample while an interaction with Nod1 and Nod2 is indicative of a peptidoglycan of Gram-negative origin in the sample.

More particularly, Nod2 is a general sensor of peptidoglycan from Gram-positive or Gram-negative bacteria through muramyl dipeptide (MDP), while Nod1 is a sensor specific for peptidoglycan from negative bacteria through MTP. Interaction between bacterial peptidoglycan and Nod proteins can be detected by the above-mentioned methods. A method for detecting interaction between MDP and Nod2 is disclosed in (S. E. Girardin et al., 2003). In a particular embodiment, the method detects bacterial peptidoglycan interaction with Nod proteins by the detection of the oligomerization of Nod1 and Nod2 by means of the FRET technology.

Furthermore, the invention encompasses methods for screening molecules that modulate bacterial peptidoglycan interaction with Nod proteins. In a particular embodiment, said method allows distinguishing molecules that specifically modulate Gram-negative peptidoglycan interaction with Nod proteins, particularly Nod1 protein. The modulation of this interaction is detected by the above-mentioned methods.

In a preferred embodiment, the invention is directed to a method for screening a molecule that modulates interaction between Gram-negative bacteria peptidoglycan and Nod1, wherein said method comprises:
 a) providing MTP;
 b) bringing said MTP into contact with Nod 1 protein in the presence and in the absence of the tested molecule;
 c) evaluating the interaction between MTP and Nod1 in the presence and in the absence of the tested molecule;

wherein a modulation of the interaction between MTP and Nod1 in the presence of the tested molecule indicates that said molecule modulates said interaction between Nod1 and Gram-negative bacteria peptidoglycan.

EXAMPLE 1

Materials and Methods

Bacterial Strains and Products

Bacterial strains used in these studies are the following: *S. typhimurium* strain C52 and C52-delta flagellin (fliC::aphA-3(Km)fljB5001::Mud(Cm)); *E. coli* K12; *S. flexneri* 5a M90T; *B. 16 subtilis* (from Agnès Fouet, Institut Pasteur); *S. aureus* (from Olivier Chesneau, Institut Pasteur); *L. casei* (from Raphaëlle Bourdet-Sicard, Danone Vitapole); *L. monocytogenes* (Strain EGD, from Pascale Cossart, Institut Pasteur); *N. meningitidis* LNP8013. Bacterial extracts were prepared from overnight cultures of bacterial strains, diluted to an OD600 of 0.3, sonicated 3 min and filtered (0.2 micron).

Commercial LPS and lipid A were from *E. coli* 0111:B4 (Sigma). Commercial *S. aureus* PGN was from Fluka Chemicals. Commercial Pam3Cys-Ser-Lys4-OH lipopeptide was from Roche Diagnostics (Mannheim) and *E. coli* lipoproteins preparations were provided by Emmanuelle Bouveret and Roland Lloubes (UPs 9027, Marseille).

Pure RE-LPS was from *E. coli* F515 and purified as previously described (P. M. Sanchez Carballo et al., Eur. J. Biochem., 261, 500, 1999). Synthetic GM-dipeptide was purchased from Sigma. PGNs of *E. coli*, *S. flexneri* and *N. meningitidis* were purified as described by Glauner et al., 1988. PGNs of *B. subtilis* and *S. aureus* were purified as described by de Jonge et al., 1992). See also Example 2.

Expression Plasmids and Transient Transfections

The expression plasmid for Flag-tagged Nod1 was from Gabriel Nuñez and has been previously described (N. Inohara et al., 1999). The HA-tagged, DN-Nod1 (117-953aa) and myc-tagged "LRR (1-644aa) Nod1 were generated by PCR and cloned into pcDNA3 (Invitrogen) and pRK5 (from Alan Hall, ICRF, London), respectively. DN-MyD88 was from Marta Muzio and the expression plasmid for vsv-tagged DN-Rip2 (7-425aa) was provided by Margot Thome and Jurg Tschopp (University of Lausanne, Switzerland). Transfections were carried out in HEK293 as previously described (S. E. Girardin et al., 2001).

NF-κB Activation Assays

For NF-κB activation assays in digitonin-permeabilized cells, 1×10⁵ HEK293 were grown in 24 well plates and then transfected for 24 h with 75 ng of NF-κB-luciferase reporter gene (19K luciferase) as previously described (S. E. Girardin et al., 2001). Cells were then incubated for 30 min at 37° C. with 25 µl of sonicated bacterial extracts in 500 µl of permeabilization buffer (50 mM HEPES, pH 7, 100 mM KCl, 3 mM MgCl2, 0.1 mM DTT, 85 mM sucrose, 0.2% BSA, ImM ATP and 0.1 mM GTP) with or without 10 µg/ml digitonin (Sigma). Permeabilization buffer was then removed and replaced with medium (DMEM, Gibco) plus 10% fetal-calf serum (Gibco) for 4 hours before processing for luciferase measurements as described previously (S. E. Girardin et al., 2001). For dominant-negative studies presented in FIG. 3, increasing amounts of dominant-negative constructs were co-transfected with the NF-κB reporter plasmid. Experiments were then performed as detailed above.

Studies examining the activation of NF-κB by LPS, lipid A, lipoproteins or the purified PGNs in cells over-expressing Nod1 were carried out as described by Inohara et al. (N. Inohara et al., 2001). Briefly, HEK293 cells were transfected overnight with 10 ng of Nod1. At the same time, the LPS, lipoproteins or peptidoglycan preparations were added and the NF-κB-dependent luciferase activation was then measured following 24 h of co-incubation. It is presumed that the transfection reagent plus the added DNA aids in the uptake of bacterial products into the cells since extracellular addition of these products to cells previously transfected and washed to remove the liposome reagent does not lead to NF-κB activation (data not shown).

NF-κB-dependent luciferase assays were performed in duplicate and data represent at least 3 independent experiments. Data show mean±SEM and are expressed as fold activation compared to vector expressing cells or as fold synergy compared to the level of NF-κB activation of Nod1-expressing cells (for 10 ng of Nod1, NF-κB activation is approximately 5 fold compared to vector-expressing cells).

For immunofluorescence studies, NF-κB activation was assessed by nuclear translocation of NF-κB p65 in HeLa, Caco-2 or isolated intestinal epithelial cells following microinjection of bacterial products (diluted 1:1 with FITC-dextran) as previously described (D. J. Philpott et al., J. Immunol., 165, 903, 2000). At least 50 microinjected cells were examined per coverslip and experiments were performed at least 2 times independently with similar results.

Interleukin-8 Production

To measure Nod1-dependent IL-8 produced in epithelial cells by muropeptides, 5×10⁵ HeLa cells were seeded into each well of a twelve well plate and transfected the following day with 10 ng Nod1 plus the individual muropeptides (as described above) or treated with IL-1 as a positive control. Eighteen hours later, supernatants were collected and assayed for IL-8 as previously described (D. J. Philpott et al., 2000) using an ELISA kit (R and D Systems).

Western Blot and Immunoprecipitations

Western blot and immunoprecipitations were carried out as previously described (S. E. Girardin et al., 2001). The Nod1 polyclonal antibody was obtained by immunization of rabbits with two peptides corresponding to aa 1-15 and 567-582 of Nod1. Serum was collected, affinity purified and verified to be specific for Nod1. The Nod2 polyclonal antibody was from Cayman Chemical (Ann Arbor, Mich.).

EXAMPLE 2

Preparation of Highly Purified PGNs from Gram-Negative and Gram-Positive Bacteria Bacterial strains used to prepare PGN are the following: *E. coli* K12; *S. flexneri* 5a M90T (wildtype); *N. meningitidis; B. subtilis* 168; *S. aureus* COL (from Olivier Chesneau, Institut Pasteur). PGNs of *E. coli* and *S. flexneri* were purified as described by Glauner et al (B. Glauner et al., 1988). PGNs of *B. subtilis* and *S. aureus* were purified as described by de Jonge et al (B. L. de Jonge et al., 1992). Briefly, bacteria were harvested in exponential growth phase at an optical density (600 nm) of 0.4-0.6 and quickly chilled in an ice-ethanol bath to minimize PGN hydrolysis by endogenous autolysins. Pellets were resuspended in ice-cold water and added drop by drop to 8% boiling SDS. Samples were boiled for 30 minutes allowing immediate inactivation of autolysins. Polymeric PGN, which is insoluble, was recovered by centrifugation and washed several times until no SDS could be detected. SDS assay was done as described by Hayashi (K. A. Hayashi, Anal. Biochem., 67, 503, 1975). SDS treatment removes contaminating proteins, non-covalently bound lipoproteins and LPS. Gram-positive bacterial samples were physically broken with acid washed glass beads (<100 nm). The PGN fraction was recovered by differential centrifugation to remove cellular debris. All PGNs were further treated with α-amylase to remove any glycogen and with trypsin (3× crystallized trypsin, Worthington) digestions to remove covalently bound proteins (LPXTG proteins in Grampositive bacteria) or lipoproteins (Gram-negative bacteria). Samples were further boiled in 1% SDS to inactivate trypsin and were washed to remove SDS. Gram-positive bacterial samples were treated with 49% hydrofluoridic acid during 48 hours at 4° C. This mild acid hydrolysis allows removal of secondary polysaccharides covalently bound to the PGN by phosphodiester bonds such as teichoic acid, capsules, poly-(β,1-6 GlcNAc), etc. Further treatment of both Grampositive and Gram-negative PGNs included washes with 8 M LiCl, 0.1 M EDTA to remove any polypeptidic contaminations and with acetone to remove lipoteichoic acids or any traces of LPS. Samples were lyophilized to measure PGN amounts. Purity of samples was assessed by HPLC amino acid and saccharide analysis after HCl hydrolysis (see also FIG. 4).

EXAMPLE 3

Analysis of *N. meningitidis* PGN by Reverse-Phase HPLC and Mass Spectroscopy

Peptidoglycans of *N. meningitidis* or *S. flexneri* were digested by the muramidase mutanolysin (M1, Sigma) to generate the entire spectrum of muropeptides for both species. The muropeptides were reduced with sodium borohydride and separated by reverse-phase HPLC as described by Glauner (B. Glauner et al., 1988). Individual muropeptide peaks were collected and directly used for biological assays. For mass spectrometry analysis, the different muropeptide fractions from *N. meningitidis* peptidoglycan were further desalted by HPLC as described by Garcia-Bustos et al. (J. F. Garcia-Bustos et al., Antimicrob. Agents Chemother., 31, 178, 1987. Desalted muropeptides were analyzed by MALDI-TOF as described by Xu et al. (N. Xu et al., Anal. Biochem., 248, 7, 1997).

These molecular masses were found for the following analyzed fractions: fraction 3 [M+H]⁺871,6214 m/z; [M+Na]⁺: 893,3633 m/z; [M+2Na-H]⁺915,3518 m/z which is consistent with the GlcNAc-MurNAc-L-Ala-D-Glu-mesoDAP structure (calculated mass 870); fraction 6 [M+H]$^+$942,4512 m/z; [M+Na]$^+$964,4689 m/z, [M+2Na-H]$^+$986,4429 m/z; [M+3Na-2H]$^+$1008,4321 m/z, which is consistent with a GlcNAc-MurNAc-L-Ala-D-Glu-mesoDAP-DAla structure (calculated mass 941); fraction 17 a mixture of two muropeptide species: 1) [M+H]$^+$851,3460 m/z; [M+Na]$^+$873,3422 m/z, [M+2Na-H]$^+$895,3219 m/z; [M+3Na-2H]$^+$917,3115 m/z which is consistent with a GlcNAc-anhydro-MurNAc-L-Ala-D-GlumesoDAP structure (calculated mass 850) and 2) [M+H]$^+$1865,5588 m/z; [M+Na]$^+$1887,5331 m/z, [M+2Na-H]$^+$1909,5753 m/z; [M+3Na-2H]$^+$1931,5625 m/z which is consistent with the muropeptide dimer GlcNAc-MurNAc-L-Ala-D-Glu-mesoDAP(GlcNAc-MurNAc-L-Ala-D-Glu-mesoDAP-D-Ala)-D-Ala structure (calculated mass 1864).

EXAMPLE 4

Nod1 Pathway

The Nod1 pathway is stimulated by commercial LPS and Gram-negative bacterial PGNs. FIG. 1A shows the stimulation of the Nod1 pathway by commercial E. coli LPS but not protein-free pure LPS or lipid A. FIG. 1B shows that lipopeptide or E. coli lipoproteins (lipidated and de-lipidated, i.e., "Lpp" and "soluble E.c Lpp") fail to activate the Nod1 pathway. FIG. 1c shows that Nod1 mediates NF-κB responsiveness to Gram-negative PGNs (E. coli, S. flexneri, N. meningitidis), but not Gram-positive PGNs (B. subtilis, S. aureus or commercial S. aureus PGN). No synergistic activation of NF-κB by E. coli PGN was observed in cells expressing ΔLRR-Nod1 as shown in FIG. 1d. LPS, lipid A, lipoproteins preparations were used at 10 μg/ml. PGN preparations were used at 1 μg/ml.

EXAMPLE 5

Characterization of the PGN Motif Detected by Nod1

The characterization of the PGN motif detected by Nod1 is shown in FIG. 2. In FIG. 2A, PGN muropeptides from N. meningitidis were separated by reverse-phase HPLC and subsequently analysed by mass spectroscopy (see supporting on-line text). N.D.(a), not determined for this particular HPLC fractionation, but found to be O-acetylated dimeric GM-tetrapeptide in subsequent HPLC fractionation and mass spectroscopy analyses. This fraction was also negative for Nod1 stimulation in additional experiments (data not shown). N.D.(b), fraction unknown. In FIG. 2B, 1% of the volume of each individual HPLC fraction was tested for stimulation of the Nod1 pathway showing that fraction 3, corresponding to GM-tripeptide, activates Nod1. Fraction 17, corresponding to a mixture of dimeric GM-tetrapeptide (does not activate Nod1) and anhydrous GM-tripeptide, activates Nod1. FIG. 2C is a schematic representation of N. meningitidis PGN detailing the Nod1-active motif from fraction 3 (GM-tripeptide) as determined by mass spectroscopy. In FIG. 2D, equivalent amounts (10 ng) of GM-dipeptide (GM-di; synthetic source), GM-tripeptide (GMtri), or GM-tetrapeptide (GM-tetra) were tested for stimulation of Nod1-, Nod2- or TLR2-dependent activation of NF-κB. FIG. 2E relates to synergistic activation of Nod1 or Nod2 by N. meningitides and B. subtilis PGNs. FIG. 2F shows the production of the pro-inflammatory chemokine, IL-8, in HeLa epithelial cells stimulated with the GM-tripeptide in the presence of Nod1 but not the GM-dipeptide or tetrapeptide. IL-1 (10 ng/ml) stimulation of IL-8 production is shown as a positive control. Buff, buffer diluent of the muropeptides.

EXAMPLE 6

Intracellular Detection of Gram-Negative Bacteria

Intracellular detection of Gram-negative but not Gram-positive bacterial products in epithelial cells through Nod1/Rip2 but not MyD88 is shown in FIG. 3.

Extracts from Gram-negative (S.t, Salmonella typhimurium; S.t ΔF, S. typhimurium-delta flagellin; E.c, Escherichia coli; S.f, Shigella flexneri) and Gram-positive (B.s, Bacillus subtilis; S.a, Staphylococcus aureus; L.c, Lactobacillus casei; L.m, Listeria monocytogenes) bacteria were added to HEK293 cells permeabilized or not by digitonin (10 μg/ml) and NF-κB activity was measured after 4 h using an NF-κB-luciferase reporter assay. The results are shown in FIG. 3A.

HeLa cells were microinjected with either Dextran-FITC only (buffer) or with bacterial extracts and stained for NF-κB p65. 100% of cell microinjected with Gram-negative bacterial supernatants show translocated in FIG. 3B, NF-κB whereas no active cells were observed with the Gram-positive bacterial supernatants. DAPI stain shows position of nuclei. Arrows point to translocated NF-κB p65 in the nuclei of activated cells.

No effect of dominant-negative MyD88 (DN-MyD88; 0, 20, 50 ng) on Gram-negative bacterial extracts-induced NF-κB activity is shown in FIG. 3c, yet inhibition of IL-1-induced NF-κB activation (IL-1, 10 ng/ml).

Inhibition of Gram-negative bacterial extracts-induced NF-κB activity in digitonin-permeabilized HEK293 cells transfected with Nod1 117-953aa (DN-Nod1; 0, 200, 400 ng) as shown in FIG. 3D.

Inhibition of Gram-negative bacterial extracts-induced NF-κB activity by dominant-negative Rip2 (DN-Rip2; 0, 50, 10 ng) as shown in FIG. 3E.

EXAMPLE 7

Response of Intestinal Epithelial Cells from Mice Deficient in Nod1

Intestinal epithelial cells from mice deficient in Nod1 do not respond to bacterial supernatants as shown in FIG. 8. Microinjection of Gram-negative but not Gram-positive bacterial supernatants activates NF-κB in isolated intestinal epithelial cells from wild-type mice, as observed by nuclear translocation of the p65 subunit of NF-κB (as described in FIG. 3B). In contrast, cells from Nod1-deficient mice are not activated by bacterial supernatants, although TNFα (10 ng/ml) can efficiently stimulate NF-κB nuclear translocation in these cells. 98% of wild-type cells microinjected with Gram-negative bacterial supernatants showed translocated NF-κB in the nucleus whereas no active cells were observed with Gram-positive bacterial supernatant microinjection. In the case of the Nod1-deficient cells, no active cells were observed in either case. Extracellular addition of either Gram-negative or Gram-positive bacterial supernatants failed to stimulate NF-κB nuclear translocation in wild-type or Nod1-deficient cells (data not shown).

In Drosophila, the Toll pathway detects both Gram-positive bacteria and fungi, while the lmd pathway is specific to Gram-negative bacterial sensing (B. Lemaitre et al., Cell, 86, 973, 1996). Recently, two peptidoglycan-recognition proteins (PGRPs) have been shown to play a key role in the discriminatory detection of bacteria in Drosophila (T. Michel et al., Nature, 414, 756, 2001; K. M. Choe et al., Science, 296, 359, 2002; M. Gottar et al., Nature, 416, 640, 2002; M. Ramet et al., Nature, 416, 644, 2002). PGRP-SA is involved in Gram-positive bacterial recognition in the Toll pathway while PGRP-LC acts upstream of lmd in Gram-negative bacterial sensing. However, definitive proof that this discriminatory detection actually relies on PGN is still lacking.

This invention has shown that in mammalian cells, Nod1-dependent detection of bacteria relies on the sensing of a Gram-negative PGN motif. Indeed, this invention demonstrates that GM-tripeptide and GM-dipeptide form a new class of bacterial PAMPs, which are recognized differentially by Nod1 and Nod2, respectively. These PGN motifs are naturally occurring degradation products released from the bacteria during growth. Therefore, the peptidic composition of the PGN degradation products either released by the bacteria or processed by the host cell in the lysosomal compartment is critical in defining the host response towards bacterial infection. In this respect, the characterization of the PGN motifs sensed by Nod1 and Nod2 suggest that these two molecules have complementary and non-overlapping functions that contribute to innate immunity. Moreover, the results of this invention have demonstrated that Nod1 is likely the sole sentinel molecule in the epithelial barrier allowing intracellular detection of bacteria through PGN sensing, thereby highlighting its key role in innate immune defense.

The invention claimed is:

1. A method for enhancing an immune response of a host, which comprises administering to the host an antigen and a composition comprising a biologically acceptable carrier and a molecule selected from (i) GlcNAc-MurNAc-L-Ala-D-Glu-mesoDAP (MTP); (ii) MurNAc-L-Ala-D-Glu-mesoDAP; (iii) L-Ala-D-Glu-mesoDAP; and (iv) the molecule in which the L-Ala of (i), (ii), or (iii) is replaced with D-Ala, wherein the molecule is administered to the host in an amount sufficient to enhance the immune response.

2. The method of claim 1, wherein the molecule is L-Ala-D-Glu-mesoDap or D-Ala-D-Glu-mesoDap.

3. The method of claim 1, wherein the molecule is GlcNAc-MurNAc-L-Ala-D-Glu-mesoDAP (MTP) or GlcNAc-MurNAc-D-Ala-D-Glu-mesoDAP.

4. The method of claim 1, wherein the molecule is MurNAc-L-Ala-D-Glu-mesoDAP or MurNAc-D-Ala-D-Glu-mesoDAP.

5. A method for inducing an immune response in a host, which comprises administering to the host a composition comprising an antigen and an adjuvant, wherein the adjuvant comprises a tripeptide having the structure L-Ala-D-Glu-mesoDAP or D-Ala-D-Glu-mesoDap and wherein the amino acid Ala of said tripeptide is not linked to a N-acylmuramic acid.

6. The method of claim 4, wherein the adjuvant comprises a tripeptide having the structure L-Ala-D-Glu-mesoDAP.

7. The method of claim 4, wherein the adjuvant comprises a tripeptide having the structure of D-Ala-D-Glu-mesoDap.

8. The method of claim 4, wherein the host is a human.

9. The method of claim 4, wherein the host is a mammal or a bird.

10. A method of vaccination in a human or animal host comprising administering to the host a composition comprising an antigen and an adjuvant, wherein the adjuvant comprises a tripeptide having the structure L-Ala-D-Glu-mesoDAP or D-Ala-D-Glu-mesoDap and wherein the amino acid Ala of said tripeptide is not linked to a N-acylmuramic acid.

11. The method of claim 10, wherein the adjuvant comprises a tripeptide having the structure L-Ala-D-Glu-mesoDAP.

12. The method of claim 4, wherein the adjuvant comprises a tripeptide having the structure of D-Ala-D-Glu-mesoDap.

13. The method of claim 10, wherein the host is a human.

14. The method of claim 10, wherein the host is a non-human animal.

15. The method of claim 10, wherein the vaccination is against a bacterial pathogen.

* * * * *